United States Patent
Tsujimoto et al.

(10) Patent No.: US 9,144,475 B2
(45) Date of Patent: Sep. 29, 2015

(54) CURABLE COMPOSITION AND CURED PRODUCT FOR DENTAL USE

(75) Inventors: Masaya Tsujimoto, Ehime (JP); Mikio Sakaguchi, Wakayama (JP)

(73) Assignees: PANASONIC HEALTHCARE CO., LTD., Ehime (JP); KAO, CORPORATION, Osaka (JP)

( * ) Notice: Subject to any disclaimer, the term of this patent is extended or adjusted under 35 U.S.C. 154(b) by 252 days.

(21) Appl. No.: 13/640,768

(22) PCT Filed: Apr. 13, 2011

(86) PCT No.: PCT/JP2011/059145
§ 371 (c)(1),
(2), (4) Date: Oct. 12, 2012

(87) PCT Pub. No.: WO2011/129356
PCT Pub. Date: Oct. 20, 2011

(65) Prior Publication Data
US 2013/0030081 A1    Jan. 31, 2013

(30) Foreign Application Priority Data
Apr. 13, 2010    (JP) ................. 2010-091982

(51) Int. Cl.
| | | |
|---|---|---|
| A61K 6/083 | (2006.01) | |
| A61C 13/087 | (2006.01) | |
| A61K 6/02 | (2006.01) | |
| C01B 33/12 | (2006.01) | |
| C01B 33/18 | (2006.01) | |
| A61K 6/00 | (2006.01) | |

(52) U.S. Cl.
CPC ............. *A61C 13/087* (2013.01); *A61K 6/0005* (2013.01); *A61K 6/0008* (2013.01); *A61K 6/0091* (2013.01); *A61K 6/0205* (2013.01); *A61K 6/083* (2013.01); *C01B 33/12* (2013.01); *C01B 33/18* (2013.01); *A61K 6/0088* (2013.01); *C01P 2002/74* (2013.01); *C01P 2004/61* (2013.01); *C01P 2004/62* (2013.01); *C01P 2006/60* (2013.01)

(58) Field of Classification Search
CPC . C01P 2002/74; A61K 6/0005; A61K 6/0088
USPC ........................................................ 523/115
See application file for complete search history.

(56) References Cited

U.S. PATENT DOCUMENTS

| 4,503,169 A | 3/1985 | Randklev |
| 4,567,030 A | 1/1986 | Yuasa et al. |
| 4,764,497 A | 8/1988 | Yuasa et al. |
| 5,883,029 A * | 3/1999 | Castle ............................ 501/33 |
| 2002/0022677 A1 | 2/2002 | Teramae et al. |
| 2005/0136176 A1* | 6/2005 | Rosenflanz et al. .......... 427/2.1 |
| 2009/0253825 A1* | 10/2009 | Ohtsuka et al. .............. 523/116 |
| 2012/0123012 A1* | 5/2012 | Rheinberger et al. .......... 522/64 |

FOREIGN PATENT DOCUMENTS

| JP | 60-233007 | 11/1985 |
| JP | 01-27976 | 5/1989 |
| JP | 01-38043 | 8/1989 |
| JP | 07-048118 | 2/1995 |
| JP | 07-206983 | 8/1995 |
| JP | 11-132421 | 5/1999 |
| JP | 2000-063636 | 2/2000 |
| JP | 2000-205523 | 7/2000 |
| JP | 2000-346318 | 12/2000 |
| JP | 2001-302429 | 10/2001 |
| JP | 2002-114620 | 4/2002 |
| JP | 2003-176120 | 6/2003 |
| JP | 3481660 | 12/2003 |

OTHER PUBLICATIONS

U.S. Appl. No. 13/640,773 to Masaya Tsujimoto et al., which was filed Oct. 12, 2012.
Savitzky et al., "Smoothing and Differentiation of Data by Simplified Least Squares Procedures", Analytical Chemistry, 36(8), Jul. 1964, pp. 1627-1639.
Sonneveld et al., "Automatic Collection of Powder Data from Photographs", J. Appl. Cryst. 8,1, 1975, pp. 1-7.
Search report from International Application No. PCT/JP2011/059145, mail date is Jul. 19, 2011.
Japanese office action in JP 2010-091982, dated May 27, 2014.

* cited by examiner

*Primary Examiner* — Michael Pepitone
(74) *Attorney, Agent, or Firm* — Greenblum & Bernstein, P.L.C.

(57) ABSTRACT

The present invention provides a curable composition allowing a cured product having high aesthetic quality, strength and durability along with having high surface lubricating property. A curable composition in the present invention comprises: an inorganic powder and a polymerizable monomer, wherein the inorganic powder contains a spherical composite powder, the spherical composite powder has a complex of silicon dioxide and at least one of alumina and zirconia, and an amorphous part and a crystalline part are mixed in the spherical composite powder. A refractive index difference is not more than 0.05 between the spherical composite powder and a cured product obtained by curing only a compound excluded the spherical composite powder.

10 Claims, No Drawings

CURABLE COMPOSITION AND CURED PRODUCT FOR DENTAL USE

CROSS REFERENCE TO RELATED APPLICATIONS

This application is a U.S. national stage application of PCT/JP2011/059145, filed Apr. 13, 2011, which claims priority to Japanese patent application 2010-091982, filed Apr. 13, 2010.

TECHNICAL FIELD

The present invention relates to a curable composition and a cured product for dental use formed from this curable composition.

BACKGROUND ART

In order to obtain teeth crown materials, prosthetic materials, artificial teeth and the like for dental use (hereafter, collectively referred to as dental materials), generally, curable composition and cured product thereof are used, containing an inorganic powder such as silica (silicon dioxide); a polymerizable monomer of the (meth)acrylate series; and a photopolymerization catalyst, a heat-curing catalyst or the like. Such dentistry materials are required to have esthetics, strength and durability for the substitution from natural teeth. In prior art, the use of a variety of inorganic powders has been proposed to confer a variety of capabilities to dental materials.

For example, the patent document 1 discloses a filler for dental composite in which silicon dioxide and another metal oxide are aggregated and then heat-treated at a lower temperature than the crystallization temperature of those oxides, to thereby form independent amorphous layers with silicon dioxide and the other metal oxide.

Patent document 2 describes a dental complex composition comprising a polymerizable monomer, a filler and a polymerization initiator, wherein a heat-treated aggregate of silica and another metal oxide, of which average particle size, refractive index, pore volume, BET specific surface area and primary particle size are controlled, is used as the filler.

Patent document 3 described a dental filling glass which contains $SiO_2$, $B_2O_3$, $Al_2O_3$, $P_2O_5$, BeO, MgO, CaO, X-ray contrasting element oxide, alkaline metal oxide, and F in specific proportions, and in which Si, B and Al elements forming the glass framework are contained at specific molar ratios.

PRIOR ART REFERENCES

Patent References

Patent document 1: Japan patent publication No. 3481660.
Patent document 2: Japan patent publication No. 2001-302429.
Patent document 3: Japan patent publication No. 2002-114620.

DISCLOSURE OF THE INVENTION

Problems to be Solved by the Invention

However, along with aesthetic quality, strength and durability, high surface lubricating property is also demanded of dental materials such that they are fixed inside the mouth cavity. Prior art dental materials, however, do not have these properties sufficiently.

In other words, with the arts described in Patent documents 1 and 2, the strength of the portion where silicon dioxide and another metal oxide are aggregated is reduced, thereby causing a problem that the strength of a resulting cured product is insufficient.

In addition, with the art described in Patent document 3, only granular type powder can be obtained as dental filling glass, and therefore a cured product of a curable composition containing such dental filling glass has the problem that the surface lubricating property becomes low.

The present invention was made in view of the above circumstances, and an object thereof is to provide a curable composition allowing a cured product having high aesthetic quality, strength and durability along with having high surface lubricating property to be formed, and a cured product for dental use obtained by curing this curable composition.

Means for Solving the Problems

A curable composition in a first invention comprises: an inorganic powder and a polymerizable monomer, wherein the inorganic powder comprises a spherical composite powder, the spherical composite powder has a complex of silicon dioxide and at least one of alumina and zirconia, an amorphous part and a crystalline part are mixed in the spherical composite powder, and a refractive index difference is not more than 0.05 between the spherical composite powder and a cured product obtained by curing only a compound excluded the spherical composite powder.

In the first invention, the spherical composite powder may have a refractive index in the range of 1.48 to 1.60.

In the first invention, the spherical composite powder may have a relative background level of 3 to 18 in X-ray diffraction spectrum.

In the first invention, the spherical composite powder may have an average particle size in the range of 0.01 to 50 μm.

In the first invention, the spherical composite powder may be obtained in a flame fusion method.

In the first invention, a polymerization catalyst may be further comprised, and the spherical composite powder content may be in the range of 5 to 95 mass %.

In the first invention, the polymerizable monomer may comprise at least one of an acrylate monomer and a methacrylate monomer, and a content of the spherical composite powder may be in the range of 55 to 95 mass %.

The cured product for dental use in a second invention is obtained by curing of the curable composition in the first invention.

Effects of the Invention

According to the present invention, it is possible to obtain a curable composition that can form a cured product with a surface lubricating property as well as high aesthetic quality, strength and durability.

Moreover, according to the present invention, it is possible to obtain a cured product for dental use with high surface lubricating property as well as high esthetic quality, strength and durability.

BEST MODE FOR CARRYING OUT THE INVENTION

In the present embodiment, the curable composition comprises an inorganic powder and a polymerizable monomer.

The inorganic powder contains a spherical composite powder. The spherical composite powder has a complex of silicon dioxide and at least one of alumina and zirconia, and the spherical composite powder has an amorphous part mixed with a crystalline part in one particle. Moreover, the refractive index difference between the spherical composite powder and the cured product obtained by curing only the compound excluded the spherical composite powder in the curable composition (hereinafter, referred as a partial cured product in order to distinguish from the cured product of the curable composition comprising the spherical composite powder) is defined as less than 0.05.

The particle form of the spherical composite powder does not need to be strictly spherical form as long as the surface is formed with a curved surface. The sphericity of particles in spherical composite powder, however, is preferably defined as at least 0.95, more preferably as at least 0.96, and yet more preferably as at least 0.97 because the spherical composite powder can be filled highly into the curable composition by improving the dispersibility of the spherical composite powder in the curable composition, because the transparency of the cured product is improved by controlling the light scattering with the spherical composite powder, and because the surface lubricating property of the cured product is improved. In regard to controlling the sphericity within the above range, with a manufacturing method described below, the sphericity can be improved by raising the firing temperature or by extending the residence time in fire.

Regarding calculation of sphericity, from the surface area of a projected cross-section and the perimeter length of this cross-section of each particle which are obtained based on microphotographic images of particles in the spherical composite powder, the value of (circumferential length of a true circle having the same area as the projected cross section area of a particle) / (a measured value of the perimeter length of the projected cross-section of a particle) is calculated. The sphericity is an average value of the values respectively derived from 50 arbitrary particles in the spherical composite powder.

The total content of silicon dioxide, alumina and zirconia within the spherical composite powder is preferably defined as at least 99.0 mass %, and more preferably as at least 99.5 mass % because the coloring of the spherical composite powder is controlled, and because the transparency of the cured product containing the spherical composite powder is improved.

The curable composition may further contain an inorganic powder other than the spherical composite powder in a range that does not compromise the effects of the present invention. As this inorganic powder other than the spherical composite powder, nano-size silica, alumina, zirconia and the like may be cited. If the inorganic powder other than the spherical composite powder is nano-sized, the transparency of the cured product for dental use is not compromised while the strength and the durability thereof are improved. From the point of view of improving the surface lubricating property of the cured product for dental use, it is desirable that the shape of the inorganic powder other than the spherical composite powder is also spherical.

The content of the spherical composite powder in the entire amount of inorganic powder is preferably defined as at least 50 mass %, more preferably as at least 75 mass %, and yet more preferably as at least 85 mass %. The upper limit of the content is 100 mass %.

For example, the spherical composite powder is obtained with a natural compound or a synthetic compound serving as raw material.

The spherical composite powder, for example, can be obtained by performing a treatment by the flame fusion method to a starting material. The flame fusion method is a method whereby the starting material such as the pulverized powder of an inorganic compound is melted in the flame and spheroidized. The starting material may be a crushed material or a spherical powder, and may also be a mixture of the crushed material and the spherical powder. By the flame fusion method, melted starting material spheroidizes due to surface tension. It is easy to obtain the spherical composite powder having an appropriate size by the flame fusion method. Furthermore, the spherical composite powder can be obtained as a complex of the silicon dioxide and at least one of alumina and zirconia by the flame fusion method. The crystalline part and the amorphous part that consist of a complex of silicon dioxide and alumina or that consist of a complex of silicon dioxide and zirconia are mixed in the spherical composite powder. Therefore, it is easy to obtain the spherical composite powder in which the amorphous part and the crystalline part are mixed.

The starting material is exemplified as a source material for silicon dioxide containing silicon; a source material for alumina containing aluminum; a mixture source material for alumina and silicon dioxide containing aluminum and silicon (a source material for alumina as well as silicon dioxide); a source material for zirconia containing zirconium; a mixture source material for zirconia and silicon dioxide containing zirconium and silicon (a source material for zirconia as well as silicon dioxide).

A source material for the silicon dioxide is exemplified as silica stone, silica sand, quart, cristobalite, amorphous silica, fumed silica, ethyl silicate, and silica sol. A material sources of alumina is exemplified as bauxite, van soil clay, aluminum oxide, aluminum hydroxide, boehmite, aluminum sulfate, aluminum nitrate, aluminum chloride, alumina sol and aluminum alkoxide like aluminum isopropoxide. A mixture source material for alumina and silicon dioxide is exemplified as Kaolin, van soil clay, bauxite, mica, sillimanite, andalusite, mullite, zeolite, montmorillonite and halloysite. A source material for zirconia is exemplified as baddeleyite, zirconium oxide and zirconium hydroxide. A mixture source material for zirconia and silicon dioxide is exemplified as zirconium silicate.

After the starting material are mixed in accordance with need or crashed after heat treatment in accordance with need, required and crushed after heat treatments as required, a treatment of the flame fusion method is applied to the start material via dispersing into the carrier gas like oxygen and putting into flame.

The flame is generated by burning oxygen and a fuel like propane, butane, methane, liquified natural gas, LPG, heavy oil, kerocine, gas oil and pulverized coal. It is preferably to employ an oxygen gas burner because of generating high-temperature flames. A structure of the burner is not especially limited, and a well-known burner, for example, disclosed in Japanese Patent Publication No. 07-48118, Japanese Patent Publication No. 11-132421, Japanese Patent Publication No. 2000-205523 and Japanese Patent Publication No. 2000-346318 can be used. By the flame fusion method, the spherical composite powder having a high sphericity can be obtained. The concentration of the starting material in the carrier gas is preferably defined in the range of 0.1 to 20 $kg/Nm^3$, and more preferably in the range of 0.2 to 10 $kg/Nm^3$ because of securing sufficient dispersibility of the starting material.

Moreover, the spherical composite powder obtained in flame fusion method may further apply heat treatment because of promoting a crystallization of the spherical composite powder and adjusting the refractive index. The heat treatment temperature is preferably defined as not more than 1700° C., more preferably as not more than 1400° C. and yet more preferably as not more than 1100° C. because of not melting the particle obtained in the flame fusion method. Additionally, the heat treatment temperature is preferably defined as at least 600° C., more preferably as at least 800° C. and yet more preferably as 1000° C. because of improving productivity by the promoting crystallization. Consequently, by summarizing above view points, the heat treatment temperature is preferably defined in a range of 600 to 1700° C., more preferably in a range of 800 to 1400° C. and yet more preferably in a range of 1000 to 1100° C. The heat treatment time relates to the heat treatment temperature. If the heat treatment temperature is high, the refractive index can be increased because the crystallization is promoted in a shorter heat treatment time. The heat treatment time is preferably defined as at least 0.01 hours, and more preferably as at least 0.5 hours because of promoting the crystallization and increasing the refractive index. The heat treatment time is preferably defined as not more than 100 hours, and more preferably as not more than 24 hours because of improving productivity. Consequently, by summarizing above viewpoints, the heat treatment time is preferably defined in a range of 0.01 to 100 hours, and more preferably in a range of 0.5 to 24 hours.

As aforementioned, the difference between the refractive index of the spherical composite powder and the refractive index of partial cured product is defined as not more than 0.05. It is especially preferable for the refractive index of the spherical composite powder to be in the range of 1.48 to 1.60. The reason is that the refractive index of the cured product for dental use made of the polymerizable monomer like an acrylate monomer and a methacrylate monomer generally is in above range.

The refractive index of the spherical composite powder is significantly influenced by the ratio between the amorphous part and the crystalline part in the spherical composite powder. Especially, when the spherical composite powder is obtained in the flame fusion method, the ratio between the amorphous part and the crystalline part in the spherical composite powder is significantly influenced by the ratio between silicon dioxide and alumina and/or zirconia in the spherical composite powder. Consequently, the refractive index tends to become larger because the crystalline part in the spherical composite powder increases by increasing the ratio of alumina and zirconia in the spherical composite powder obtained in the flame fusion method.

The relative background level in the X-ray diffraction spectrum of the spherical composite powder becomes as an indicator of the ratio between the amorphous part and the crystalline part in the spherical composite powder. When the relative background level becomes larger, an existence ratio of the amorphous part becomes larger in the spherical composite powder. In contrast, when the relative background level becomes smaller, an existence ratio of the crystalline part becomes larger in spherical composite powder.

The relative background level is expressed as a ratio (F/A) between a background level of the X-ray diffraction spectrum of the spherical composite powder (F) and a background level of the X-ray diffraction spectrum of a crystalline standard sample (A) when each X-ray diffraction spectra of the spherical composite powder and the standard sample is measured under the same condition. The background level is the average value of a diffraction intensity of a background part in the X-ray diffraction spectrum.

The background level (F) of the spherical composite powder is derived from the following mathematical formula (I), based on the powder x-ray diffraction spectrum measured using a Cu—Kα beam.

[Math 1]

$$F = \frac{\sum_{2\theta=10}^{35} (\text{Diffraction Intensity})}{N} \quad (1)$$

The denominator N in the right member of the above mathematical formula (1) is a number of points in measurement of the diffraction intensity of the background part in the range of 2θ=10 to 35°, and the number is 1501. The numerator on the right side of the above mathematical formula (1) shows the sum total of the diffraction intensity in each of the 1501 points of the measurement.

The background level (A) of the standard sample can be derived in the same method as the case of the spherical composite powder when a standard alumina powder, for example, (National Institute of Standard & Technology, Standard Reference Material 674a) is used as the standard sample.

The value (F/A) obtained by dividing the background level (F) of the spherical composite powder by the background level (A) of the standard sample derived as described above is the relative background level.

When the ratio between silicon dioxide, alumina and/or zirconia is adjusted at obtaining the spherical composite powder in the flame fusion method, the refractive index of the spherical composite powder can be easily adjusted by adjusting the relative background level of the spherical composite powder. It is preferable for the relative background level to be not more than 18, more preferable to be not more than 15, and yet more preferable to be not more than 10 because of adjusting the refractive index of the spherical composite powder to at least 1.45. Moreover, it is preferable for the relative background level to be at least 3, more preferable to be at least 5, and yet more preferable to be at least 7 because of improving transparency of the spherical composite powder and reducing the wear and contamination of forming die at the time of forming the curable composition. In short, it is preferable for the relative background level to be in the range of 3 to 18, more preferable to be in the range of 5 to 15, and yet more preferable to be in the range of 7 to 10.

The ratio between silicon dioxide, alumina and/or zirconia is appropriately adjusted so that the spherical composite powder has a desired refractive index. This ratio is adjusted by changing the composition of the starting material, for example, when the spherical composite powder is obtained in the flame fusion method. Since the refractive index is adjusted in a predetermined range, the mass ratio of a total amount of alumina and zirconia to silicon dioxide contained in the spherical composite powder is preferably defined as not more than 1, and more preferably as not more than 0.9. Since the mass ratio and/or the refractive index are adjusted in a predetermined range, above mass ratio of a total amount is preferably defined as at least 0.1, and more preferably as at least 0.2. By summarizing above view points, it is preferable for the mass ratio of a total amount of alumina and zirconia to silicon dioxide contained in the spherical composite powder to be not more than 1, more preferable to be in the range of 0.1 to 1, yet more preferable to be in the range of 0.2 to 0.9, and yet more preferable to be in the range of 0.4 to 0.9.

It is preferable for an average particle size of the spherical composite powder to be in the range of 0.01 to 50 µm. When the average particle size of the spherical composite powder is at least 0.01 µm, a viscosity rise of the curable composition containing the spherical composite powder is suppressed and it is also possible for the spherical composite powder to be combined in large quantities in the curable composition without causing viscosity rises of the curable composition. As a result, the strength of the cured product of the curable composition is further improved. And, when the average particle size of spherical composite powder is not more than 50 µm, the surface lubricating property of the cured product is further improved. Incidentally, the average particle size is D50 (the medium particle size that an accumulation of volume becomes to 50% of the total cumulative volume) measured by the laser diffraction/dispersion method. It is preferable for the average particle size of the spherical composite powder to be 0.1 to 20 µm, and especially preferable to be 1 to 10 µm. In order to control the average particle size of the spherical composite powder in above range, the particle size of material particle for putting into flame may be adjusted in the manufacturing method described below.

It is preferable for the refractive index of the spherical composite powder to be in the range of 1.48 to 1.60, and more preferable to be in the range of 1.49 to 1.59 because of improving the transparency of cured product containing the spherical composite powder by approximating the refractive index of the spherical composite powder to the refractive index of the cured product of the compound excluded the spherical composite powder. For controlling the refractive index in above range in the manufacturing method described below, when the mass ratio between alumina and zirconia; and silicon dioxide ([alumina+zirconia]/silicon dioxide) of the starting material is increased or the particle obtained in the flame fusion method is further applied the heat treatment, the refractive index can be raised.

It is preferable for the spherical composite powder to be applied a surface treatment by a coupling agent. Incidentally, the coupling agent can be combined by mixing with the curable composition. In the case of the spherical composite powder contained in the curable composition to obtain a dental material, it is preferable to use a general coupling agent for dental use. The coupling agent is exemplified as a well-known coupling agent like γ-methacryloxypropyltrimethoxysilane and vinyl trimethoxysilane.

The curable composition contains the polymerizable monomer. In particular, the polymerizable monomer contained in the curable composition to obtain the dental material is exemplified as a well-known polymerizable monomer like acrylate monomers, methacrylate monomers, urethane acrylate monomers, urethane methacrylate monomers, acrylate monomers containing a bisphenol A skeleton, and methacrylate monomers containing a bisphenol A skeleton. These polymerizable monomers is specifically exemplified as a chemical compound like methyl acrylate, methyl methacrylate, 2-hydroxyethyl acrylate, 2-hydroxyethyl methacrylate, . triethylene glycol diacrylate, triethyleneglycol dimethacrylate, di (phenyl glycidyl ether acrylate)-hexamethylene diurethane, di-2-methacryloxy ethyl-2,2,4-trimethyl hexamethylene diurethane(UDMA), 2,2-bis(4-(3-methacryloyloxy-2-hydroxypropoxy)phenyl)propane(Bis-GMA), trimethylolpropane triacrylate, and trimethylolpropanetrimethacrylate. Either only one kind of these compounds or several of them in combination may be used.

Moreover, epoxy resin monomer compounds like bisphenol A diglycidyl generally used for electronic material use may be used as the polymerizable monomer.

The curable composition may contain a polymerization catalyst in accordance with request. In particular, the polymerization catalyst to obtain a dental material is exemplified as a well-known polymerization catalyst for dental use like thermal polymerization initiators and photo polymerization initiators. The polymerization catalyst is specifically exemplified as the thermal polymerization initiator like benzoyl peroxide, tertiary butyl peroxide, and methyl ethyl ketone peroxide; and the photo polymerization initiator like camphorquinone, benzoin, and benzophenone. Either only one kind of these compounds or several of them in combination may be used.

The curable composition may further contain a polymerization inhibitor, an antioxidant, an ultraviolet absorber, a photo stabilizer, an antimicrobial, a fluorine sustained-release tablet, a colored pigment, and other well-known additive agent. A proper compound generally used for dentistry are employed as an additives agent contained in the curable composition to obtain the dental material.

It is preferable for the content of the spherical composite powder in the curable composition to be in the range of 5 to 95 mass %. In this way, when the content of the spherical composite powder is at least 5 mass %, a reinforcement effect of the cured product is started expressing by the inorganic powder, and when this content is not more than 95 mass %, it becomes easy to mix the entire composition homogeneously. It is more preferable for the content of the spherical composite powder to be in the range of 49 to 95 mass %, and yet more preferable to be in the range of 55 to 95 mass %.

The cured product is obtained when such curable composition undergoes a photo-curing or a thermal-curing. The refractive index difference is not more than 0.05 between the spherical composite powder in the cured product and the partially cured product because the amorphous silicon dioxide and the crystalline silicon dioxide are mixed in this cured product as aforementioned. Consequently, the cured product obtained from the curable composition becomes to have a sufficiently high transparency.

Moreover, while the refractive index of silicon dioxide is lower than the refractive index of the cured product of general polymerizable monomer for dental use, the refractive index of alumina and zirconia is higher than the refractive index of the cured product of general polymerizable monomer for dental use. Consequently, the refractive index of the spherical composite powder can be easily approached to the refractive index of the cured product of the polymerizable monomer, when the composition ratio between the silicon dioxide and the alumina and zirconia is adjusted. Thus, even in the case that the composition of anything other than the spherical composite powder in curable composition is changed, the cured product having high transparency can be obtained, when the spherical composite powder having an appropriate refractive index is used. When the refractive index difference between the partially cured product and the spherical composite powder becomes to smaller, the transparency of cured product becomes to higher.

It is preferable for the transparency of the cured product for dental use to be in the range of 40% to 95%, more preferable to be in the range of 50% to 95%, and yet more preferable to be in the range of 60% to 95%, according to the evaluation in the transparency test mentioned below.

Moreover, since the spherical composite powder is a spherical form powder, the surface lubricating property of the cured product becomes higher. Consequently, it becomes difficult that the oral cavity and teeth are given damage, even when the cured product is fitted in the oral cavity.

Moreover, since the spherical composite powder of a high homogeneity is contained in the cured product, the cured product can become to have a high intensity and durability, comparing to the case that heterogeneous particles are agglutinated in the cured product.

Moreover, since silicon dioxide, alumina and zirconia have a high safety to a living organism, the cured product also becomes to have a high safety to the living organism. Furthermore, when the spherical composite powder containing a complex of zirconia is used, the cured product can become to have the x-ray contrast property.

Since the cured product formed from the curable composition has an advantage mentioned above, the cured product can be preferably used as the cured product for dental use to form, for example, a crown material, a prosthetic material, and an artificial teeth. Consequently, the curable composition can be preferably used in order to form the cured product for dental use. Especially, when the refractive index difference is not more than 0.02 between the partially cured product and the spherical composite powder, the cured product for dental use can be obtained and have a very close transparency to natural teeth. It is preferable for this refractive index difference to be not more than 0.01.

It is preferable for the curable composition for forming the cured product for dental use that the content of the spherical composite powder is in the range of 55 to 95 mass %, and that at least one of an acrylate monomer and a methacrylate monomers are contained as the polymerizable monomer. In this case, when the content of the inorganic powder is at least 55 mass %, the cured product becomes to have a sufficient intensity and durability for using as artificial teeth and dental prosthesis. Moreover, since acrylate monomers have a lot of successful records of use as a dental material, acrylate monomers have a high safety in the case of using as dental material to living organism.

The cured product for dental use is formed as an appropriate form like prismatic, cylindrical, placoid or discoid form; or as a prosthetic appliance like an artificial tooth, an inlay, a crown. The prosthetic appliance for dental use like an artificial tooth, an inlay and a crown are manufactured from the cured product for dental use like prisms, columns, angle plates and circular plates by milling in CAD/CAM devices.

The method to form the cured product for dental use is described below. When the curable composition is given a photo irradiation, a heat or both the photo radiation and heat adapting to the curable composition, the curable composition is cured by the polymerization. Thereby, the cured product for dental use is obtained.

For example, in the case that the curable composition contains a heat polymerizable initiator, after the curable composition is filled in the cavity of the forming die having an appropriate shape like a prismatic form, a cylindrical form, a placoid form, a discoid form, an artificial tooth, an inlay or a crown, air bubbles are removed from the curable composition by reduced pressure in the cavity. Next, the curable composition undergoes polymeric curing under pressurization or a normal pressure in the state that the cavity of the forming die is closed by a lid. Thereby, the cured product for dental use is obtained. The applied pressure and the heating temperature at polymeric curing may be changed with time in accordance with need.

When the curable composition contains a photo polymerizable initiator, it needs to prepare the forming die and the lid which include a part having photo transparency. Herein, the forming die has the cavity for prismatic, cylindrical, placoid or discoid form; or has the cavity for an artificial tooth, an inlay or a crown. After the curable composition is filled in the cavity of this forming die, air bubbles are removed from the curable composition by reduced pressure in this cavity. Next, the curable composition is given the photo irradiation under the pressurization or the normal pressure in the state that this forming die is closed by the lid. Thereby, the curable composition undergoes polymeric curing and the cured product for dental use is obtained. At the polymeric curing, the curable composition after the photo irradiation can be applied a heat treatment as a post-curing treatment in accordance with need.

A material of the forming die and the lid which include a part having photo transparency is exemplified as stainless steel, Teflon (registered trademark), silicon, glass, PET and polycarbonate, but it should not be limited above. A surface of the forming die and the lid is preferably applied an adhesion treatment of a mold release agent.

In addition, although the curable composition is preferably used in order to form the cured product for dental use, the curable composition can be preferably used for an electronic material like sealant, adhesive agent and laminating board forming material, too.

EXAMPLES

[Production of powder]
(Powder A)
The alumina (purity: 99.9%) of 50 parts by mass and the silicon dioxide (purity: 99.9%) of 50 parts by mass were dried in vacuum after mixing them within ethanol. A powder obtained in this way were heated at 1400° C. for 4 hours, and the pulverized powder was obtained by crushing until the average particle size became to 5.3 μm after the heat treatment. Next, the flames of about 2000° C. were generated by using oxygen as the carrier gas and burning LPG at the ratio versus oxygen (volume ratio) of 1.1, and the powder were obtained by supplying the pulverized powder above into the flame. Finally, powder A was obtained by further heat treatment to above powder at 1100° C. for 24 hours.

(Powder B)
The alumina (purity: 99.9%) of 40 parts by mass and the silicon dioxide (purity: 99.9%) of 60 parts by mass were dried in vacuum after mixing them within ethanol. A powder obtained in this way was heated at 1400° C. for 4 hours, and the pulverized powder was obtained by crushing until the average particle size became to 4.6 μm after the heat treatment. Next, the flames of about 2000° C. were generated by using oxygen as the carrier gas and LPG at the ratio versus oxygen (volume ratio) of 1.1. Powder B was obtained by supplying the pulverized powder above into this flame.

(Powder C)
The silicon dioxide (purity: 99.9%) of 90 parts by mass and the zirconia (purity: 99.9%) of 10 parts by mass were dried in vacuum after mixing them within ethanol. A powder obtained in this way was heated at 1400° C. for 4 hours and the pulverized powder was obtained by crushing until the average particle size became to 3.9 μm after the heat treatment. Next, the flames of about 2500° C. were generated by using oxygen as the carrier gas and LPG at the ratio versus oxygen (volume ratio) of 1.1. Powder C was obtained by supplying the pulverized powder above into this flame.

(Powder D)
The silicon dioxide (purity: 99.9%) of 90 parts by mass, the alumina (purity: 99.9%) of 5 parts by mass and the zirconia (purity: 99.9%) of 5 parts by mass were dried in vacuum after mixing them within ethanol. A powder obtained in this way was heated at 1400° C. for 4 hours and the pulverized powder was obtained by crushing until the average particle size became to 4.1 μm after the heat treatment. Next, the flames of about 2500° C. were generated by using oxygen as the carrier gas and LPG at the ratio versus oxygen (volume ratio) of 1.1. Powder D was obtained by supplying the pulverized powder above into this flame.

(Powder E)

The silicon dioxide (purity: 99.9%) were crushed until the average particle size became to 4.9 μm and a pulverized powder was obtained. Next, the flames of about 2000° C. were generated by using oxygen as the carrier gas and burning LPG at the ratio versus oxygen (volume ratio) of 1.1. Powder D was obtained by supplying the pulverized powder above into this flame.

[Evaluation of Powder]

(Composition)

About each of powders A to E, a composition of each of powders A to E was determined the quantity by elemental analysis in the fluorescence X-ray method (JIS R2216 "Methods for X-ray fluorescence spectrometric analysis of refractory bricks and refractory mortar").

(Relative Background Level)

Each of powders A to E was filled in a glass holder, and the powder x-ray diffraction spectrum of each of the powders A to E was measured using the Kα beam from Cu with an automatic x-ray diffractometer (Model No. RINT2500) manufactured by Rigaku Corporation. The obtained diffraction spectrum was smoothed by the methods described in the literature (Abraham Savitzky et. al., Analytical Chemistry, 36(8), 1627 (1964)) with the condition of 25 points. Next, the background portion of the diffraction spectrum was extracted by methods described in the literature (Sonneveld, E. J and Visser, J. W., J. Appl. Cryst. 8, 1 (1975)) with the conditions of 40 points interval and 32 times iterations. Based on the results thereof, background level (F) of the powder was calculated based on the above mathematical formula (1).

Meanwhile, using a standard alumina powder (National Institute of Standard & Technology, Standard Reference Material 674a) as a standard sample, powder x-ray diffraction spectrum of this standard alumina powder was measured with the same conditions as in the case of powders A to E. Furthermore the background level (A) of the standard alumina powder was calculated by the same method as in the case of powders A to E.

The relative background levels (F/A) of each powders A to E were calculated by dividing the background levels (F) of powders A to E calculated as described above by the background level (A) of the standard alumina powder.

(Average Particle Size)

D50 (the medium particle size that an accumulation of volume becomes to 50% of the total cumulative volume) of each powders A to E was measured by the laser diffraction/dispersion method using Model No. LA-920 manufactured by HORIBA, Ltd. The average particle size was measured by dispersing the particle in the ion-exchange water while the supersonic wave was applied in the state that the transmittance of the dispersed liquid was in the range of 80 to 90%. The relative refractive index was not used in the measurement.

(Sphericity)

Each of powders A to E was observed by using a real surface view microscope (model number VF-7800) by KEYENCE CORPORATION. The projected cross section area of the particle and the perimeter length of this cross section about arbitrary 50 particles were measured from each images taken. Subsequently, the value of (circumferential length of a true circle having the same area as the projected cross section area of a particle)/(a measured value of the perimeter length of the projected cross section of a particle) was calculated in each of 50 particles. The average value from obtained values was decided as the sphericity.

(Refractive Index)

The refractive index of each of the powders A to D was determined by the method B (immersion method using a microscope (Becke line method)) among the JIS K7142 "Methods for the determination of refractive indices of plastics".

Above results are shown in [Table 1] below.

TABLE 1

| | | Powder A | Powder B | Powder C | Powder D | Powder E |
|---|---|---|---|---|---|---|
| Composition (parts by mass) | Silicon dioxide | 50 | 60 | 90 | 90 | 100 |
| | Alumina | 50 | 40 | — | 5 | — |
| | Zirconia | — | — | 10 | 5 | — |
| Refractive index | | 1.57 | 1.53 | 1.55 | 1.51 | 1.44 |
| Average particle size (μm) | | 5.7 | 4.8 | 5.3 | 5.5 | 5.1 |
| Relative background level | | 5.3 | 9.1 | 12 | 11 | 24 |
| Sphericity | | 0.99 | 0.99 | 0.98 | 0.98 | 0.98 |

Examples 1 to 6 and Comparative Example 1

(Preparation of the curable composition and the cured product)

The curable composition in each of examples and comparative example was obtained by mixing the compounds shown in Table 2 below. Incidentally, TEDM, PGA-HMU, TMPTM and BPO in Table 2 mean triethyleneglycol dimethacrylate, di(phenylglycidylether acrylate)-hexamethylene diurethane, trimethylolpropane trimethacrylate, and benzoylperoxide, respectively. Moreover, the surface treatment was applied to powders A to E by mixing after spraying a silane coupling agent (γ-methacryloxypropyl trimethoxysilane). The amount for using of the silane coupling agent was 0.4 parts by mass with respect to 60 parts by mass of powder.

In Examples 1, 2, 4 to 6 and Comparative Example 1, a curable composition was filled into the forming die of stainless (two types of cavity sizes: 50 mm×40 mm×2 mm and 50 mm×40 mm×1 mm), degassed by reduced pressure, and then a stainless lid was fitted onto this forming die. In this state, the curable composition was cured by being heated at 80° C. for 1 hour and then heated at 120° C. for 1 hour to obtain a cured product.

In Example 3, the curable composition was filled into the forming die made of a glass plate and a stainless frame (two types of cavity sizes: 50 mm×40 mm×2 mm and 50 mm×40 mm×1 mm), degassed by reduced pressure, and then a stainless lid was fitted onto this forming die. In this state, a 365 nm UV light with an intensity of 100 mW/cm² was irradiated for 5 minutes from a dental photopolymerization device towards the curable composition through the glass surface on one side of the forming die and then was irradiated for 5 minutes through the glass surface on the opposite side of the forming die. In so doing, the curable composition was cured to obtain the cured product.

A test piece was cutout from the cured product obtained in each of the examples and comparative example, and evaluation tests of this test piece were carried out by the methods described in the following.

(Bending Strength Test (Normal State))

The dimensions of the test piece were 25 mm×2 mm×2 mm, and the strength at break of this test piece was measured using a bending testing machine at 1 mm per minute cross-head speed. In each examples and comparative example, measurements were performed on 5 test pieces, and evaluation was by the mean value of the results thereof. This value served as a representative value for the strength of the cured product.

(Bending Strength Test (after Water Immersion))

The dimensions of the test piece were 25 mm×2 mm×2 mm, and this test piece was first immersed in water at 37° C. for 24 hours. Next, the strength at break of this test piece was measured by using a bending testing machine at 1 mm per minute cross-head speed. In each examples and comparative example, measurements were performed on 5 test pieces, and evaluation was by the mean value of the results thereof. This value served as a representative value for the durability of the cured product.

(Refractive Index Difference)

In each examples and comparative example, a curable composition was prepared without mixing powders A to E, and this curable composition was cured to obtain a cured product (partially cured product). The refractive index of this partially cured product was determined by the method A (measurement method using an Abbe refractometer) among the JIS K7142 "Methods for the determination of refractive indices of plastics". For each examples and comparative example, the difference between the refractive index of this partially cured product and the refractive index of the powder was calculated.

(Transparency Test)

The dimensions of the test piece were 13 mm×13 mm×1 mm. This test piece was buffed until the thickness reached 0.8 mm. The total light transmittance of this test piece was measured with a hazemeter, with the total light transmittance of the air space being 100%. In each examples and comparative example, measurements were performed on 3 test pieces, and evaluation was by the mean value of the results thereof. This value served as a representative value for the aesthetic quality of the cured product.

(Evaluation Results)

The above results are shown in Table 2 below.

TABLE 2

| | | | Example | | | | | | Comparative example |
|---|---|---|---|---|---|---|---|---|---|
| | | | 1 | 2 | 3 | 4 | 5 | 6 | 1 |
| Powder species | | | Powder A | Powder B | Powder B | Powder B | Powder C | Powder D | Powder E |
| Composition (parts by mass) | Powder | | 72 | 72 | 72 | 72 | 72 | 72 | 72 |
| | TEDM | | 14 | 14 | 14 | 10 | 14 | 14 | 14 |
| | PGA-HMU | | 14 | 14 | 14 | 9 | 14 | 14 | 14 |
| | TMPTM | | | | | 9 | | | |
| | BPO | | 0.2 | 0.2 | | | 0.2 | 0.2 | 0.2 |
| | Camphorquinone | | | | 0.3 | | | | |
| Evaluation | Bending strength test (normal state) | MPa | 195 | 191 | 182 | 185 | 187 | 187 | 190 |
| | Bending strength test (after water immersion) | MPa | 177 | 172 | 168 | 165 | 175 | 171 | 173 |
| | Refractive index of partially cured product | — | 1.53 | 1.53 | 1.53 | 1.52 | 1.53 | 1.53 | 1.53 |
| | Refractive index difference | — | 0.04 | 0.00 | 0.00 | 0.01 | 0.02 | 0.02 | 0.09 |
| | Transparency test | % | 40 | 65 | 63 | 62 | 55 | 55 | 27 |

The cured product obtained in each examples demonstrated sufficient strength, durability and aesthetic quality. When used as dental materials such as crown material, prosthetic material, and artificial teeth for dental use, these cured products have excellent properties as substitution materials for natural teeth.

The invention claimed is:

1. A process of producing a curable composition comprising:
   an inorganic powder and
   a polymerizable monomer,
   wherein
   the inorganic powder contains a spherical composite powder,
   the spherical composite powder has a complex of silicon dioxide and at least one of alumina and zirconia,
   an amorphous part and a crystalline part are mixed in the spherical composite powder,
   the sphericity of particles in the spherical composite powder is defined as at least 0.95, and
   a refractive index difference is not more than 0.05 between the spherical composite powder and a cured product obtained by curing only a compound excluded the spherical composite powder, and
   the process comprises:
   obtaining the spherical composite powder in a flame fusion method, and
   obtaining the curable composition by mixing the inorganic powder containing the spherical composite powder with the polymerizable monomer.

2. The process of producing a curable composition according to claim 1, wherein the spherical composite powder has a refractive index in the range of 1.48 to 1.60.

3. The process of producing a curable composition according to claim 1, wherein the spherical composite powder has a relative background level of 3 to 18 in X-ray diffraction spectrum.

4. The process of producing a curable composition according to claim 1, wherein the spherical composite powder has an average particle size in the range of 0.01 to 50 μm.

5. The process of producing the curable composition according to claim 1, further comprising a polymerization catalyst, wherein the spherical composite powder content is in the range of 5 to 95 mass %.

6. The process of producing a curable composition according to claim 1, wherein the polymerizable monomer contains at least one of an acrylate monomer and a methacrylate monomer, and a content of the spherical composite powder is in the range of 55 to 95 mass %.

7. A process of production of a cured product for dental use, the process comprising:
  producing the curable composition by process of producing a curable composition according to claim 1, and
  forming the curable composition as defined in claim 1 to the cured product for treatment of a tooth.

8. The process of production the curable composition according to claim 1, further comprising:
  subjecting the spherical composite powder to a heat treatment.

9. The process of producing a curable composition according to claim 8, wherein a heat treatment temperature in the heat treatment is defined as not more than 1700°C.

10. The process of producing a curable composition according to claim 8, wherein a heat treatment time in the heat treatment is defined as at least 0.01 hours.

* * * * *